(12) United States Patent
Nordt, III

(10) Patent No.: US 6,602,216 B1
(45) Date of Patent: Aug. 5, 2003

(54) PLANTAR FASCIA TENSION DEVICE

(75) Inventor: William E. Nordt, III, 7601 Forest Ave., Suite 228, Richmond, VA (US) 23229

(73) Assignee: William E. Nordt, III, Richmond, VA (US)

( * ) Notice: Subject to any disclaimer, the term of this patent is extended or adjusted under 35 U.S.C. 154(b) by 0 days.

(21) Appl. No.: 09/768,276

(22) Filed: Jan. 25, 2001

Related U.S. Application Data (60) Division of application No. 09/302,513, filed on Apr. 30, 1999, which is a continuation-in-part of application No. 09/080,260, filed on May 18, 1998, now abandoned.

(51) Int. Cl.[7] .................................................. A61F 5/00
(52) U.S. Cl. .............................. 602/28; 602/30; 602/65
(58) Field of Search .......................... 602/5, 23, 27–30, 602/60–62, 65–66; 128/882; 482/79; 36/8.3, 97, 132, 136, 11; 601/23, 27

(56) References Cited

U.S. PATENT DOCUMENTS

| | | | | |
|---|---|---|---|---|
| 1,788,852 A | | 1/1931 | Arthur ........................... | 602/66 |
| 2,110,890 A | * | 3/1938 | Paul .............................. | 36/8.3 |
| 2,305,926 A | | 12/1942 | Kohler ..................... | 128/893 X |
| 3,027,658 A | * | 4/1962 | Rigsby ........................... | 36/2.5 |
| 3,213,551 A | * | 10/1965 | Krauss .......................... | 36/97 |
| 3,568,338 A | * | 3/1971 | Nadler ........................... | 36/11 |
| 3,713,437 A | | 1/1973 | Weidmer ...................... | 602/28 |
| 4,538,599 A | | 9/1985 | Lindemann ................... | 602/23 |
| 4,559,934 A | | 12/1985 | Philipp ......................... | 128/80 |
| 4,596,387 A | * | 6/1986 | Roberts ........................ | 272/93 |
| 4,998,722 A | * | 3/1991 | Scott ............................ | 272/96 |
| 5,144,694 A | * | 9/1992 | Conrad Da oud et al. ........ | 2/69 |
| 5,257,969 A | | 11/1993 | Mance .......................... | 602/28 |
| 5,361,411 A | * | 11/1994 | Bohn et al. ..................... | 2/69 |
| 5,361,517 A | * | 11/1994 | Liener ........................ | 36/72 R |
| 5,382,224 A | | 1/1995 | Spangler ....................... | 602/23 |
| 5,399,155 A | | 3/1995 | Strassburg et al. ............. | 602/28 |
| 5,472,411 A | | 12/1995 | Montag et al. ................. | 602/23 |
| 5,554,107 A | | 9/1996 | Shannahan .................... | 602/66 |
| 5,718,673 A | | 2/1998 | Shipstead .................... | 602/27 |
| 5,887,591 A | | 3/1999 | Powell et al. ............... | 128/882 |

FOREIGN PATENT DOCUMENTS

FR 08705580 * 4/1987 .................... 36/97

\* cited by examiner

*Primary Examiner*—Denise M. Pothier
(74) *Attorney, Agent, or Firm*—Swidler Berlin Shereff Friedman, LLP

(57) ABSTRACT

A static tension device for retaining the greater toes in a dorsiflexed position to treat plantar fasciitis, while not restricting the ankle. The toes are retained in a dorsiflexed position by a tension strap and optionally, a relief in the tension strap allows the lesser toes remain in a non-dorsiflexed position. An optional stabilization strap aids in maintaining the position of the tension strap, especially when the user is ambulatory. An optional slipper aids in maintaining the position of the tension strap, especially when the user is at rest.

8 Claims, 9 Drawing Sheets

PLANTAR FASCIA TENSION DEVICE

This is a divisional of prior application Ser. No. 09/302,513, filed Apr. 30, 1999, which is a continuation-in-part of U.S. patent application Ser. No. 09/080,260, filed May 18, 1998 now abandoned.

FIELD OF THE INVENTION

The present invention relates generally to a foot tension device, and more particularly, to a static tension device that retains toes in a dorsiflexed position to treat the disorder known as plantar fasciitis.

BACKGROUND OF THE INVENTION

The plantar fascia acts as a "bowstring" between the medial tuberosity of the heel bone and the metatarsals in the forefoot. The plantar fascia helps maintain the longitudinal arch height of the foot. When the toes are dorsiflexed (hyper extended) the plantar fascia tightens. This tightening process is known as the "windlass effect."

Plantar fasciitis, also known as heel spurs, is a common ailment resulting from inflammation of the plantar fascia. Plantar fasciitis results in inflammatory degeneration and heel pain when the foot bears weight. Treatment for this disorder commonly includes stretching the plantar fascia. Historically, this was achieved through physical manipulation of the foot.

More recently, treatment includes night splinting. Since the resting tone of the foot flexors exceeds that of the extenders, the foot tends to be in a plantar flexed position during sleep. This results in a shortening of the plantar fascia, which exacerbates the condition and often results in the affected person awakening with extremely sensitive heels. Existing night splints maintain some tension on the plantar fascia throughout the night by retaining the ankle in a dorsiflexed position. While this technique may provide some relief, the retention of the ankle is not required and may detract from the effectiveness of the treatment.

The dorsiflexion of the toes, that is the windlass effect, is the primary cause of plantar fasciitis. Thus, it is preferred that splinting be aimed solely at the forefoot rather than also incorporating the ankle in the treatment.

Thus, a need exists for a plantar fascia tension device to treat plantar fasciitis that retains the toes in a dorsiflexion position without restricting the ankle.

SUMMARY OF THE INVENTION

The present invention is a night splinting device for the purpose of ameliorating the symptoms of plantar fasciitis which maintains some or all of the toes in a dorsiflexed position at the metatarsal-phalangeal joints. Thus, a plantar fascia tension device can implement the windlass effect. The present invention achieves this without confining or restricting the ankle joint, which remains substantial free.

The present invention consists of a tension strap that wraps circumferential around the foot. It extends under the toes and around the heel. Thus, some or all of the toes are held in a comfortable degree of dorsiflexion. The tension strap is adjustable so that various sizes of feet can be accommodated by the same tension strap. The strap may be secured by an attachment device such as Velcro, tape, or other means for securing the strap.

An optional relief in the tension strap prevents bunching of the toes by allowing the lesser toes (e.g. the third, fourth and fifth toes) to extend through the relief. This relief is desirable because the windlass effect is primarily a function of the first and second toes. The benefit of the tension device is not substantially reduced by allowing the lesser toes to remain non-dorsiflexed. Additionally, the user can more easily ambulate while wearing the tension device with an optional relief.

An optional second strap (stabilization strap) may be used to stabilize the tension strap. The stabilization strap crosses the tension strap near the mid-foot perpendicular to the tension strap. The stabilization strap can be adjusted such that one size accommodates a variety of size of feet. Additionally, the optional stabilization strap may be adjusted to provide direct pressure on the plantar fascia as it crosses the bottom of the foot. The stabilization strap can be fixedly attached to the tension strap to form a single device.

The tension strap can be used while the user is sleeping or during other periods of rest.

An optional slipper may be used to hold the tension strap in place. Preferably, the tension strap is attached to the sole of the slipper. The slipper includes an attachment device at the rear of the slipper to receive one end of the tension strap.

Other advantages and salient features of the invention will become apparent from the following detailed description, which taken in conjunction with the annexed drawings, discloses the preferred but non-limiting embodiment of the invention.

BRIEF DESCRIPTION OF THE DRAWINGS

The present invention is illustrated by way of example and not limitation in the accompanying figures in which like reference numerals indicate similar elements and in which.

DETAILED DESCRIPTION OF THE PREFERRED EMBODIMENT

Figure 1A:
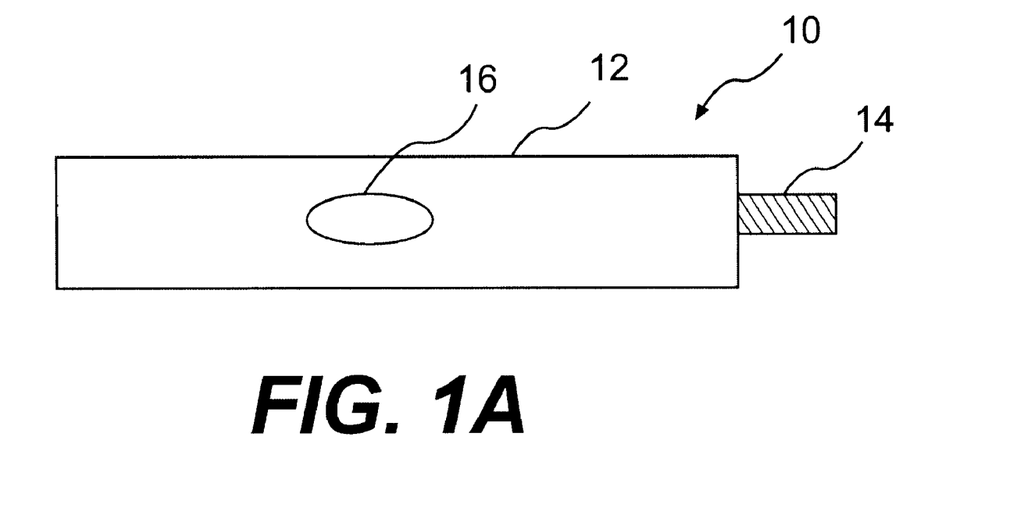
FIGS. 1A and 1B illustrate a plantar fascia tension device, including an optional stabilization device.

FIG. 1A shows a tension device 10 in a flat position. The tension device 10 includes a tension strap 12 and an attachment device 14. The tension strap 12 can be made from a variety of materials, such as canvas, cotton, foam rubber, etc. It is desirable that the tension strap 12 be longer than the circumference of the users foot, such that the tension strap 12 can overlaps itself. For example, a tension strap that is approximately 26 inches long can circumscribe a human foot up to approximately ten inches long and three inches wide. The height of the tension strap 12 can vary depending upon the size of the foot it is used on. In a preferred embodiment, the tension strap 12 is from one to six inches in height.

The attachment device 14 of the tension device 10 secures the tension strap 12 in place. The attachment device 14 can include Velcro, snaps, tape, buttons, or other means for securing the tension strap 12 in place. It is desirable that the attachment device 14 is reusable and adjustable. In a preferred embodiment, the attachment device 14 is a piece of Velcro approximately two inches by four inches that is permanently attached near an end of the tension strap 12. If the tension strap 12 is made of material receptive to Velcro, then no mating piece of Velcro is required. If, however, the tension strap 12 is not receptive to mating, the attachment device 14 can include a mating device attached to the tension strap 12 at an appropriate location. The attachment device 14 preferably allows the tension strap 12 to be adjusted to accommodate a variety of feet sizes.

The tension strap 12 can optionally contain a relief 16. The relief 16 can accommodate one or more of the lesser toes in a comfortable, non-dorsiflexed position. The size and shape of the relief 16 can vary depending on the dimensions of the user's foot. The relief 16 can be rectangular, elliptical, oval, or irregularly shaped. In a preferred embodiment, the relief 16 is a generally oval shape approximately one inch high and two inches wide.

Figure 1B:
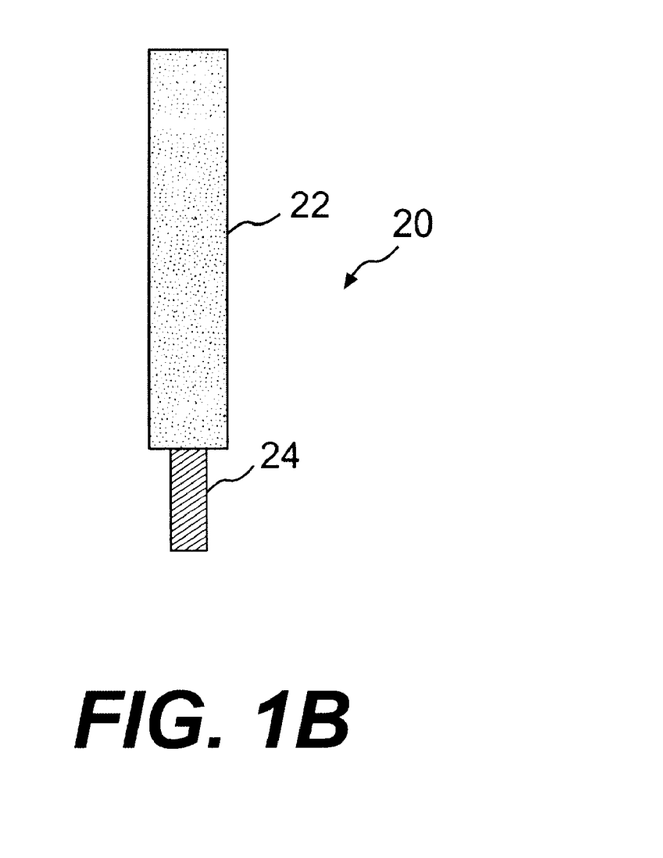

FIG. 1B shows an optional stabilization device 20. The optional stabilization device 20 includes a stabilization strap 22 and an attachment device 24. The stabilization strap 22 can be made from a variety of materials, similar to those described as appropriate for the tension strap 12. It is desirable that the stabilization strap 22 be longer than the cross-sectional circumference of the foot, such that the stabilization strap 22 can overlap itself. The size of the stabilization strap 22 can vary depending on the size of the foot. In a preferred embodiment, the stabilization strap 22 is approximately two inches wide and approximately 16 inches long. It is understood that the stabilization strap 22 can be from approximately 0.5 to six inches wide and between approximately ten and 22 inches long.

The attachment device 24 on the stabilization device 20 is similar to the attachment device 14 on the tension device 10. However, the attachment device 24 on the stabilization device 20 may be relatively smaller. For example, the attachment device 24 can be a one by three inch piece of Velcro. In a preferred embodiment, the attachment device 24 is reusable and adjusts the length of the stabilization strap 20.

Figure 2A:
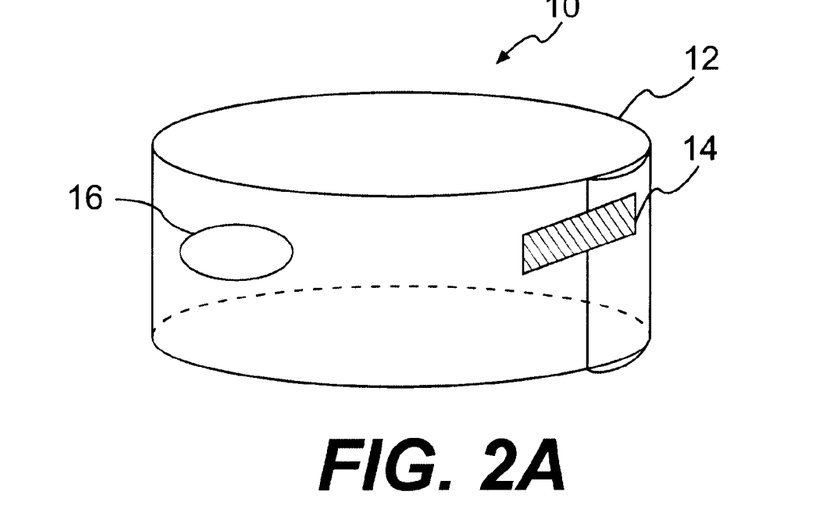
FIGS. 2A and 2B illustrate the plantar fascia tension device of FIG. 1A and 1B in an application configuration.

FIG. 2A shows the plantar fascia tension device 10 of FIG. 1A in a user configuration. The tension strap 12 is wrapped around the users foot (not shown), such that the tension strap 12 overlaps itself. The attachment device 14 secures the tension strap 12 in place. The optional relief 16 allows a number of the lesser toes to remain in a non-dorsiflexed position.

Figure 2B:
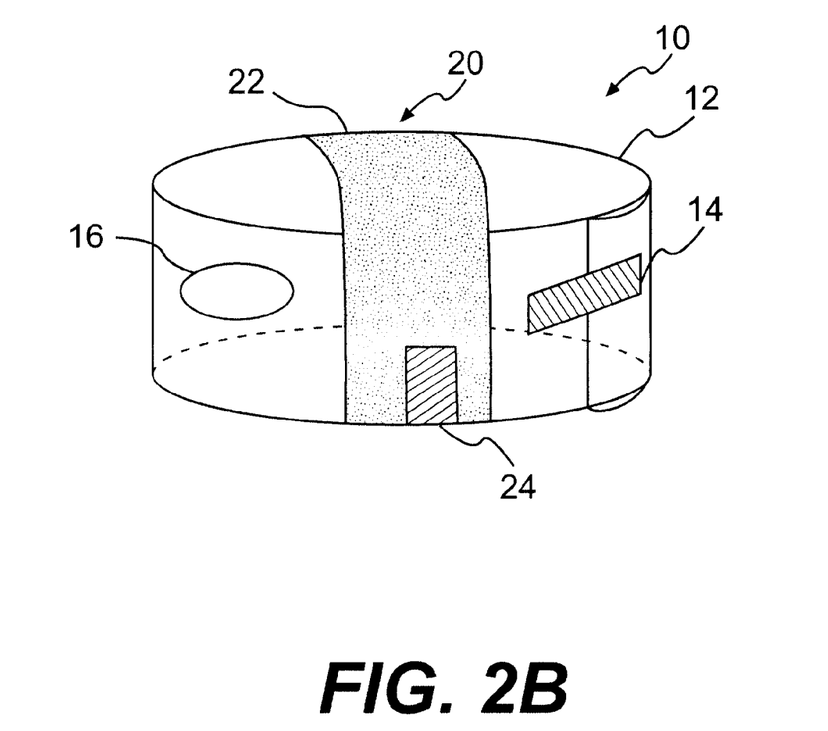

FIG. 2B shows the plantar fascia tension device 10 with the optional stabilization device 20 in a user configuration. The optional stabilization strap can be permanently secured, temporarily secured, or free floating relative to the tension strap 12. The stabilization device 20 overlaps itself and is secured by attachment device 24.

Figure 3:
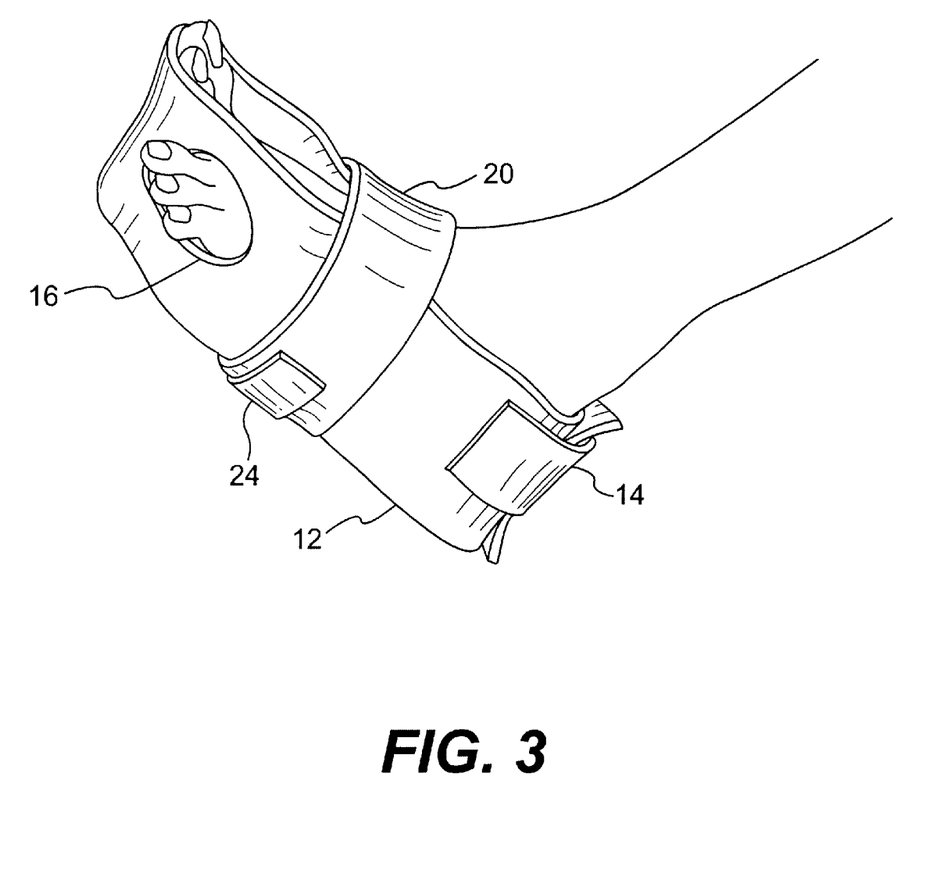
FIG. 3 illustrates the plantar fascia tension device and a human foot with the two greater toes dorsiflexed.

FIG. 3 shows the tension device 10 including the optional relief 16 and the optional stabilization strap 20 in a user configuration around a foot 30. The two greater toes are shown in a dorsiflexed position and the three lesser toes protrude through the optional relief 16. As illustrated, the ankle is not restricted.

The tension device 10 provides support to the toes without restricting the movement of the ankle. Thus, the users retains near full medial and lateral movement of the ankle joint (subtalar joint) while using the tension device 10.

The tension device 10 when used to treat plantar fasciitis, can be worn during the night or other periods reduced activity.

Figure 4:
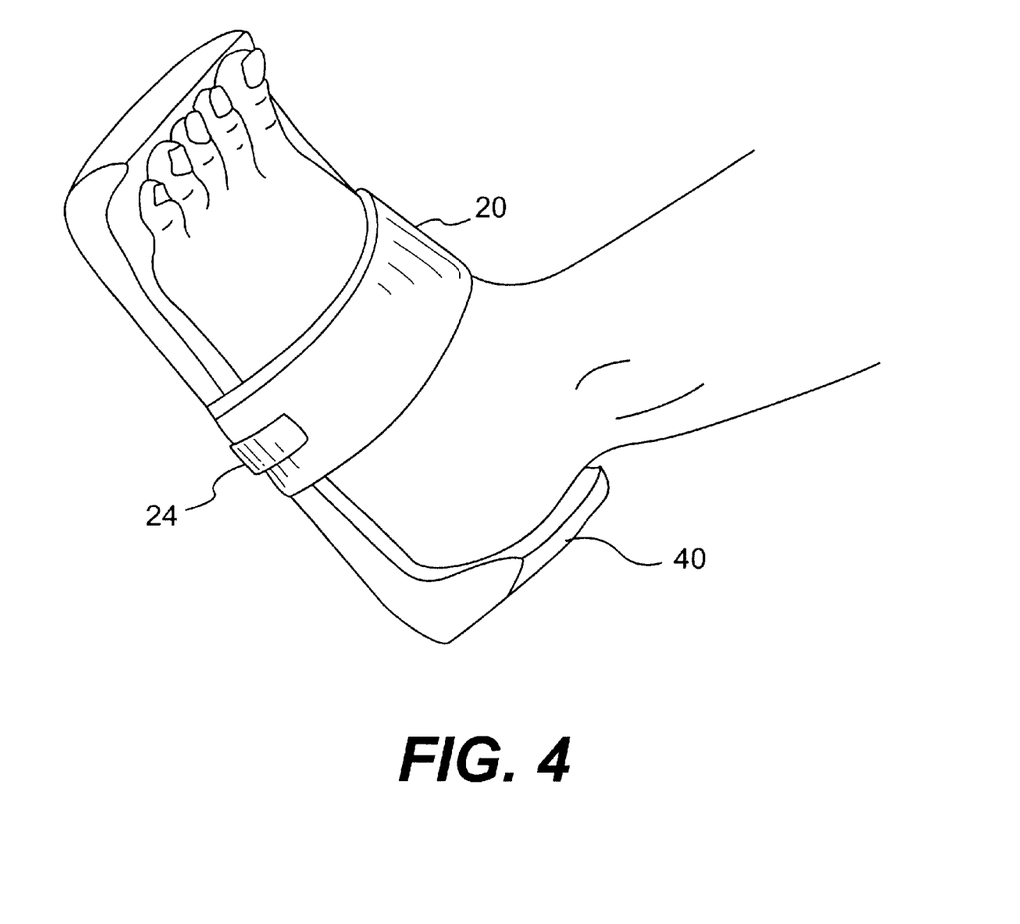
FIG. 4 illustrates a platform embodiment of the plantar fascia tension device and a human foot.

FIG. 4 illustrates a platform embodiment of the plantar fascia tension device. In this embodiment, a platform 40 maintains a number of the greater toes in the dorsiflexed position. The stabilization strap 20 retains the platform 40 is a stable position relative to the foot. The stabilization strap 20 is removeably fixedly attached by means of attachment device 24. While the illustrated embodiment of the platform embodiment shows all five toes in the dorsiflexed position, this embodiment is not so limited. The platform in this embodiment could retain one, two, or more toes in the dorsiflexed position. The greater toes being the dorsiflexed while the lesser toes being non-dorsiflexed.

Figure 5:
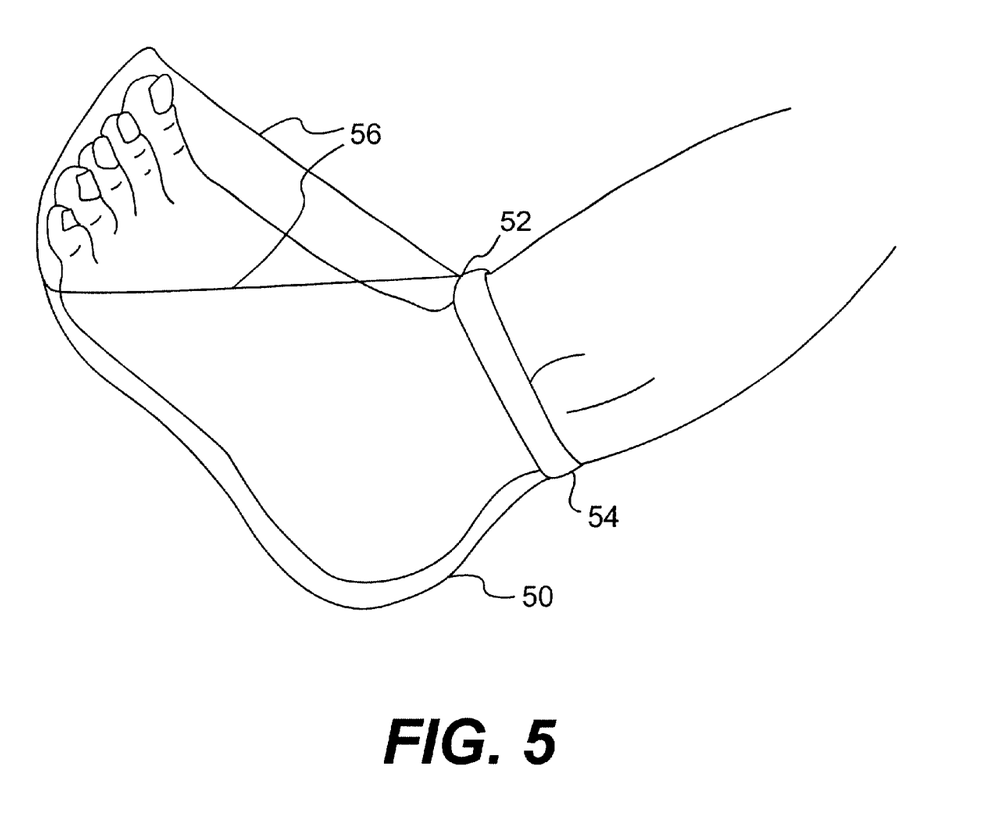
FIG. 5 illustrates a sock embodiment of the plantar fascia tension device and a human foot.

FIG. 5 illustrates a sock embodiment of the plantar fascia tension device. A sock 50 includes a band 54 that is below the ankle. The sock 50 optionally includes adjustable tension straps 56 that attach near the toe of the sock 50 and at the front of the band 54. While the illustrated embodiment of the sock embodiment shows all five toes in the dorsiflexed position, this embodiment is not so limited. The sock in this embodiment could retain one, two, or more toes in the dorsiflexed position. The greater toes being the dorsiflexed while the lesser toes being non-dorsiflexed. in the versions of this embodiment where less than all the toes are dorsiflexed, a relief in the sock could allow the lesser toes to remain non-dorsiflexed. Alternatively, the sock could be so constructed as to allow the lesser toes to remain non-dorsiflexed without the a relief in the sock. The optional tension straps 56 support the toe portion of the sock in a manner that maintains the desired toes in a dorsiflexed position. When the tension straps are adjustable, the amount of dorsiflexion of the toes can be adjusted as the course of treatment requires.

Figure 6:
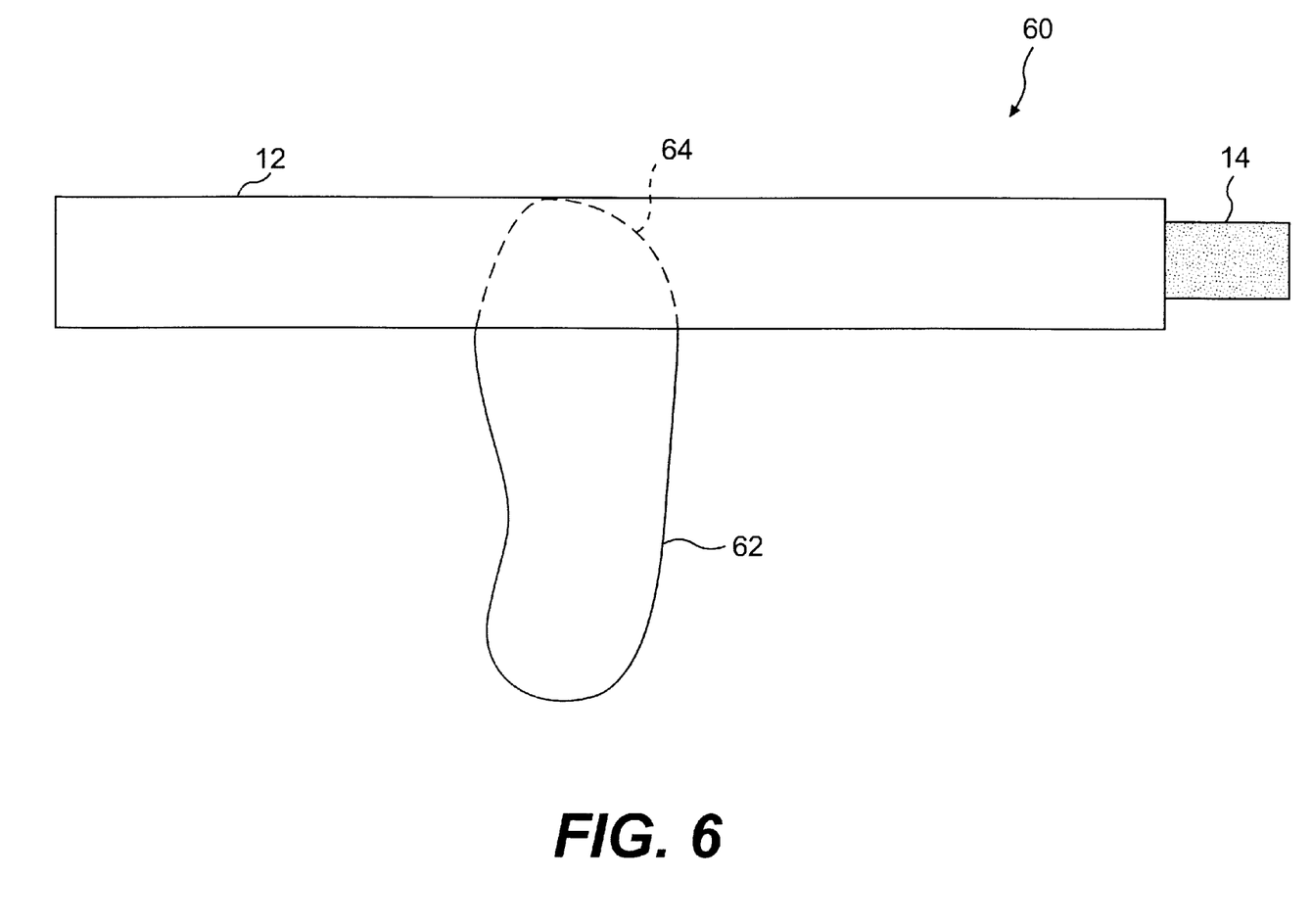
FIG. 6 is a bottom view of a plantar fascia tension device according to another embodiment of the present invention.

FIGS. 6, 7, 8, and 9 illustrate a slipper embodiment of the plantar fascia tension device 60. FIG. 6 is a bottom view of device 60. Plantar fascia tension device 60 includes slipper 62 and a tension strap 12. In a preferred embodiment, slipper 62 is a comfortable slipper, such as a bedroom slipper. Tension strap 12 and attachment device 14 were described above. In a preferred embodiment, tension strap 12 is fixedly and permanently attached near its midpoint to slipper 62. Preferably the attachment is accomplished by stitching tension strap 12 to the sole of slipper 62, as shown by stitching 64.

Figure 7:
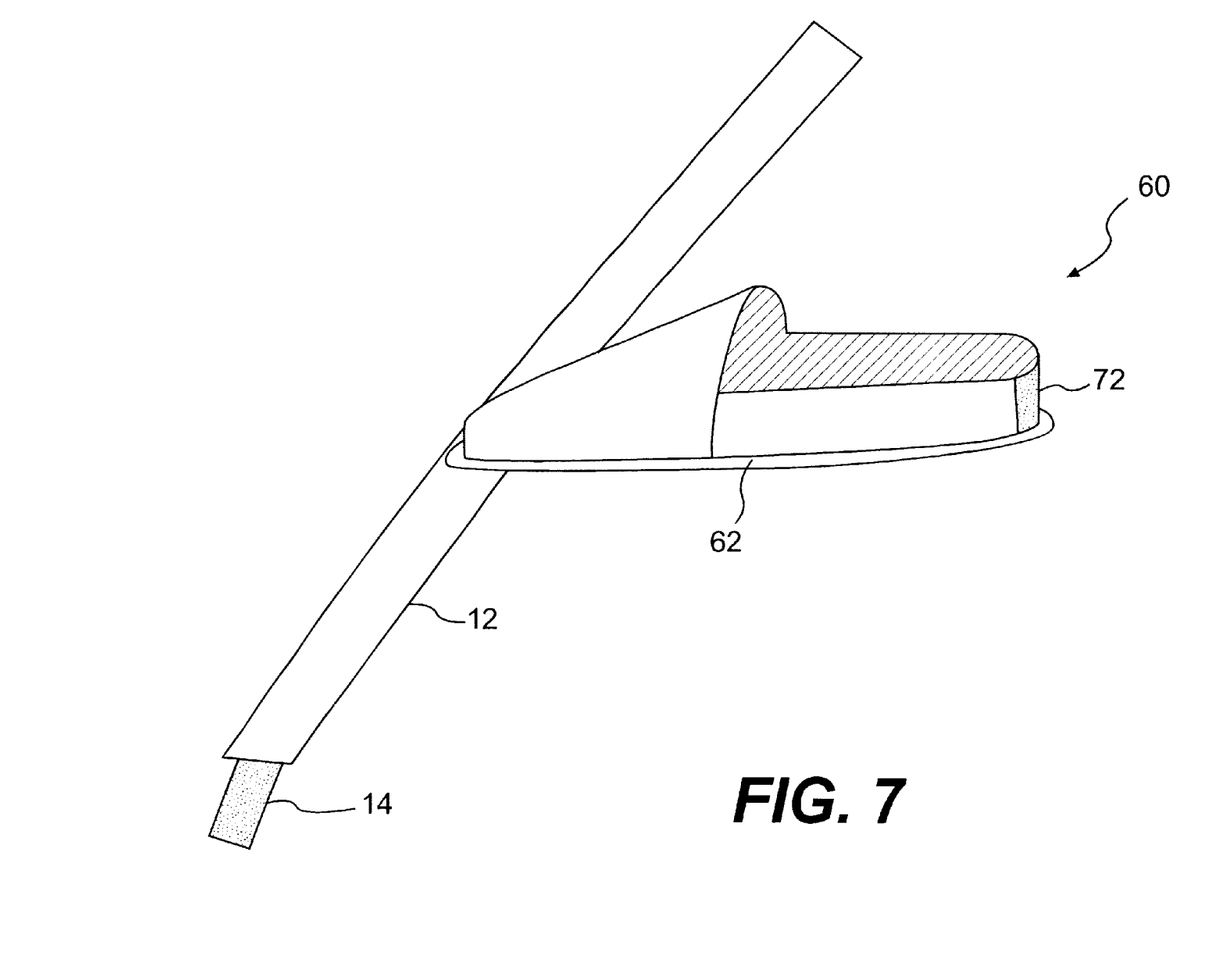
FIG. 7 is a perspective view of the plantar fascia tension device of FIG. 6.

FIG. 7 is a perspective view of plantar fascia tension device 62. Referring to FIG. 7, slipper 62 optionally includes attachment device 72, preferably located at the rear of the slipper. Attachment device 72 is similar to attachment device 14.

Figure 8:
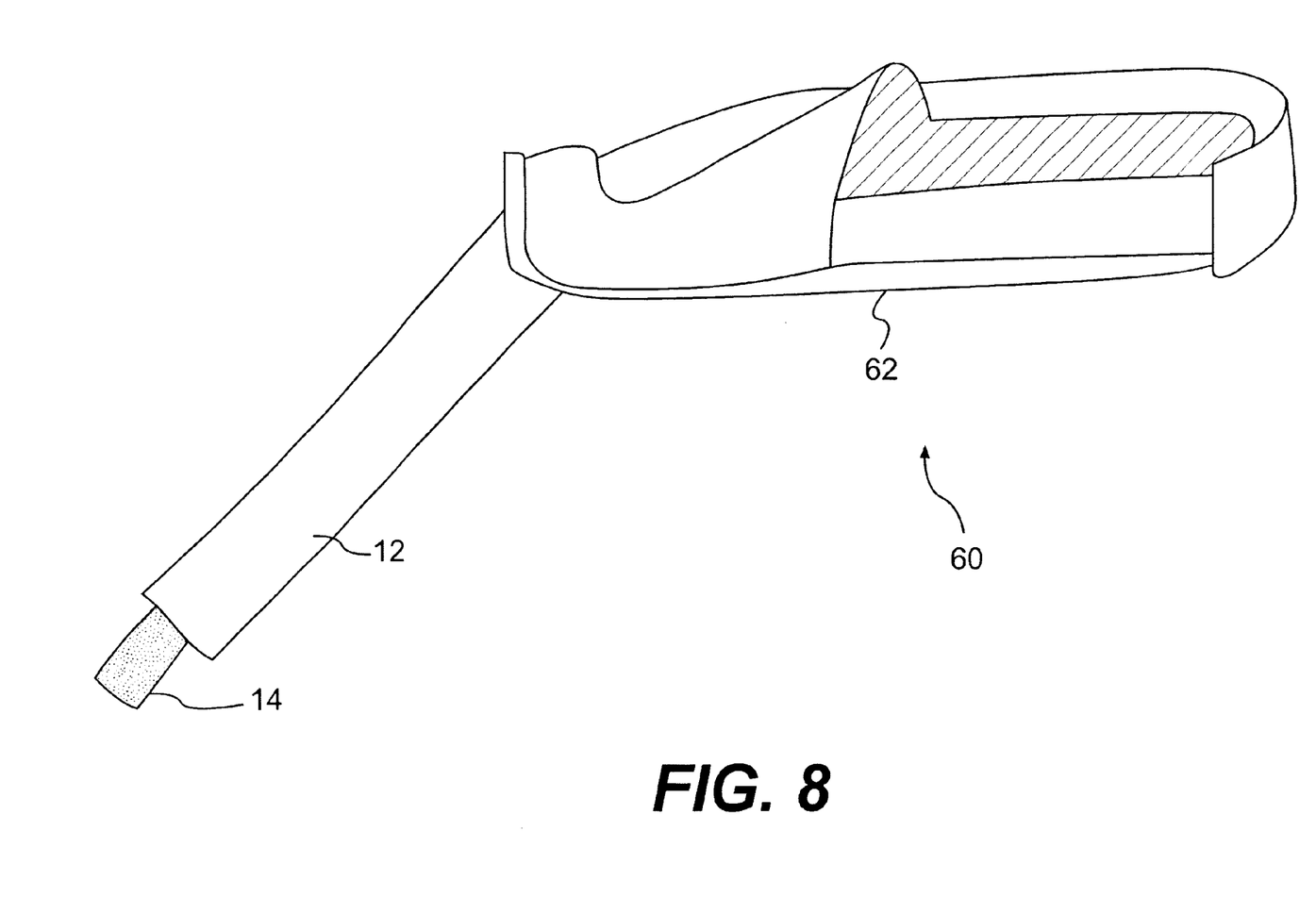
FIG. 8 is a perspective view similar to FIG. 7, except that the tension strap is shown in a partially deployed position.

FIG. 8 is a perspective view of plantar fascia tension device 60 where an end of tension strap 12 has been wrapped around slipper 62 and attached to attachment device 72, resulting in partial dorsiflexion of one or more toes of the foot.

Figure 9:
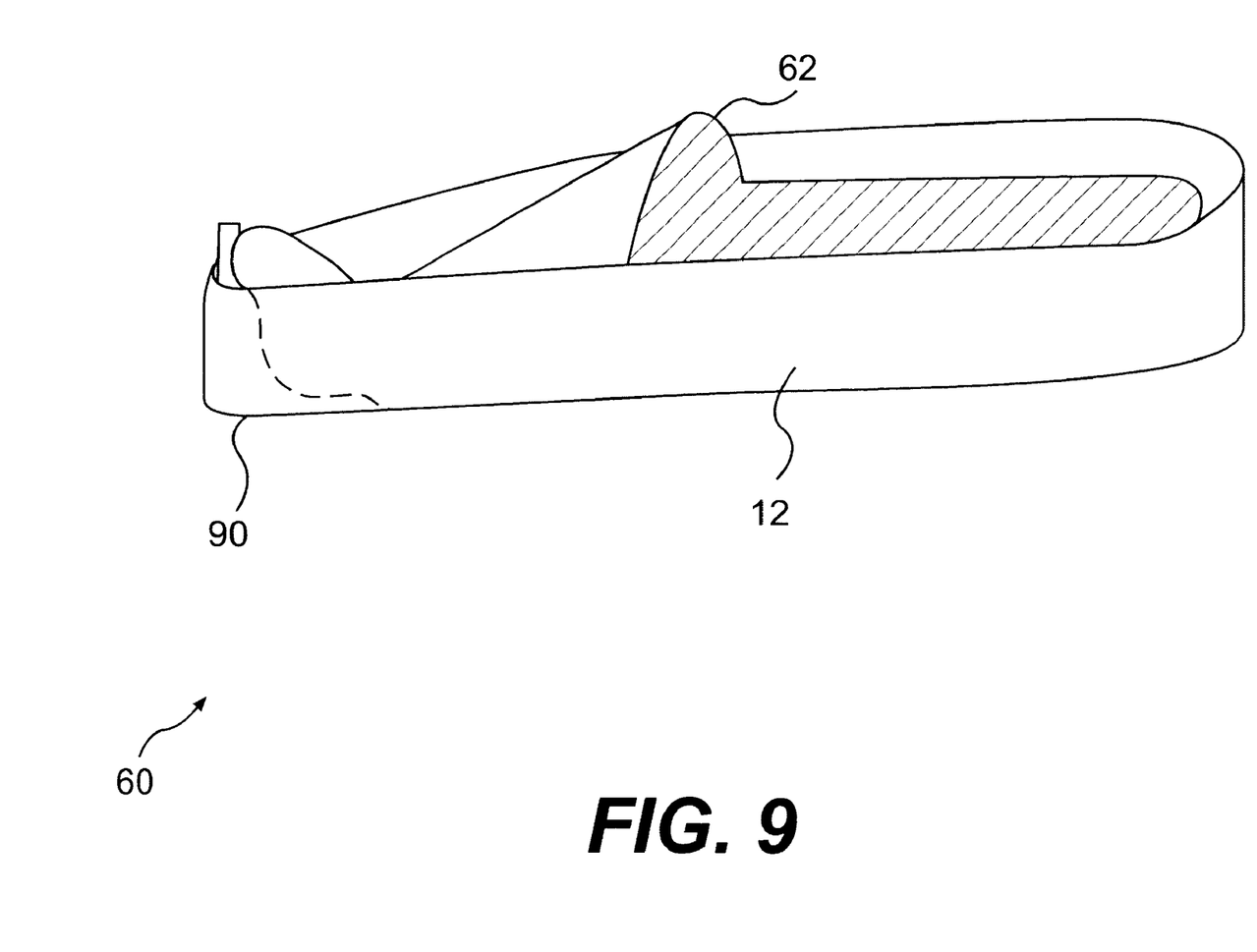
FIG. 9 is a perspective view similar to FIGS. 7 and 8, except that the tension strap is shown in a fully deployed position.

FIG. 9 is a perspective view of plantar fascia tension device 60 where both ends of tension strap 12 have been wrapped around slipper 62, resulting in dorsiflexion of one or more toes of the foot, as shown by dotted line 90.

The slipper embodiment described above is ideal for maintaining the tension strap in position, especially when the user is at rest.

While preferred embodiments have been shown and described, it will be understood that it is not intended to limit the disclosure, but rather it is intended to cover all modifications and alternate methods and apparatuses falling within the spirit and scope of the invention as defined in the appended claims or their equivalents.

What is claimed is:

1. An apparatus for treating plantar fasciitis comprising:
   a slipper having a substantially planar sole portion and a foot retaining portion, the foot retaining portion having an opening at an open ankle portion, an enclosed toe portion and a heelward portion, the sole portion having a toe end and a heel end;
   a tension strap fixedly connected to the toe end, the tension strap having a first free end and a second free end;
   an adjustable fastener fixedly connected to the tension strap, the adjustable fastener securing the first free end of the tension strap to the tension strap near the second free end of the tension strap to form a loop sized and configured to circumscribe the slipper horizontally between the toe portion and the heelward portion, the loop having a length which maintains at least one toe in a dorsiflexed position; and
   a second adjustable fastener on the heelward portion of the slipper, the second adjustable fastener securing the tension strap to the heelward portion of the slipper.

2. The apparatus for treating plantar fasciitis according to claim 1, wherein the tension strap includes two opposite axial end portions and a medial portion, the tension strap connected to the toe end at the medial portion.

3. The apparatus for treating plantar fasciitis according to claim 1, wherein the adjustable fastener is selected from the group consisting of tape, snaps, and buttons.

4. The apparatus for treating plantar fasciitis according to claim 1, wherein the adjustable fastener is at least one of: complementary microhooks and complementary microloops.

5. The apparatus for treating plantar fiasciitis according to claim 1, wherein the adjustable fastener is connected to the tension strap at an end portion.

6. The plantar fascia tension device according to claim 1, further comprising the second adjustable fastener fixedly connected to the heelward portion of the slipper.

7. An method for treating plantar fasciitis comprising:
   providing a slipper having a substantially planar sole portion and a foot retaining portion, the foot retaining portion having an open ankle portion, an enclosed toe portion and a heel portion, the sole portion having a toe end and a heel end;
   providing a tension strap fixedly connected to the toe end, the tension strap sized and configured to circumscribe the slipper horizontally between the toe portion and the heel portion;
   providing an adjustable fastener fixedly connected to the tension strap;
   placing a foot in the slipper at the open ankle portion;
   circumscribing the slipper with the tension strap between the toe portion and the heel portion to place at least one toe in a dorsiflexed position; and
   securing the adjustable fastener to maintain the at least one toe in the dorsiflexed position.

8. The method for treating plantar fasciitis according to claim 7, wherein placing the foot is performed at a period of reduced activity for the foot.

* * * * *